United States Patent [19]

Despreaux et al.

[11] 4,301,246
[45] Nov. 17, 1981

[54] PROCESS FOR CHENODEOXYCHOLIC ACID PRODUCTION

[75] Inventors: Carl Despreaux, Cedar Grove; Thomas A. Narwid, Pompton Plains; Norberto J. Palleroni, North Caldwell; Milan R. Uskokovic, Upper Montclair, all of N.J.

[73] Assignee: Hoffmann-La Roche Inc., Nutley, N.J.

[21] Appl. No.: 113,019

[22] Filed: Jan. 18, 1980

Related U.S. Application Data

[62] Division of Ser. No. 29,420, Apr. 12, 1979, Pat. No. 4,230,625.

[51] Int. Cl.$^3$ .............................................. C12P 33/06
[52] U.S. Cl. ...................................... 435/58; 435/911
[58] Field of Search .......................................... 435/58

[56] References Cited

U.S. PATENT DOCUMENTS 3,047,470  7/1962  Pruess et al. ........................... 435/60
3,539,449  11/1970 Marx et al. ............................. 435/58
4,220,716  9/1980  Fujiwara et al. ...................... 435/58

Primary Examiner—Alvin E. Tanenholtz
Attorney, Agent, or Firm—Jon S. Saxe; Bernard S. Leon; James H. Callwood

[57] ABSTRACT

A multi-step synthesis of chenodeoxycholic acid from 3-keto-bisnorcholenol, a compound readily obtained from the abundant plant sterol β-sitosterol, is described. A key step in the synthesis is the stereoselective microbial introduction of the 7-alpha hydroxy group into 3-keto-bisnorcholenol.

5 Claims, No Drawings

PROCESS FOR CHENODEOXYCHOLIC ACID PRODUCTION

This is a division of application Ser. No. 29,420, filed Apr. 12, 1979, now U.S. Pat. No. 4,230,625.

BACKGROUND OF THE INVENTION

Chenodeoxycholic acid has exhibited valuable therapeutic activity, particularly as an agent for dissolution of cholesterol gallstones. This compound is currently obtained from cholic acid. An exemplary synthesis starting from cholic acid is described in U.S. Pat. No. 3,836,550. However, this process is of limited importance due to the circumstances which exist regarding the natural sources of cholic acid which is extracted from cow bile or with some additional processing from chicken bile. Calculations based on estimated demand for chenodeoxycholic acid assuming only one-third the potential patients utilize this drug indicate that such natural sources even if utilized to maximum potential could provide only a minor portion of such demand. Thus, an efficient synthesis from highly abundant starting materials is an important factor in determining whether chenodeoxycholic acid achieves its potential role in medicine.

Hydroxylation at the 7-position of compounds in the androstane and pregnane series is well known in the art. An early report by Kramli and Horvath, Nature, 4120, 619 (1948) indicated the 7-hydroxylation of cholesterol by incubation with Proactinomyces roseus was carried out but the actual configuration of the product was not determined. Well documented reports of 7-alpha-hydroxylation on the following substrates appear in the art:

- deoxycorticosterone—Meystre et al., Helv. Chim. Acta 38, 381(1955).
- progesterone and related compounds—U.S. Pat. No. 2,753,290, U.S. Pat. No. 2,836,608, McAleer et al., J. Org. Chem. 23, 958 (1958).
- testosterones—U.S. Pat. No. 2,801,251, U.S. Pat. No. 2,960,436, Irmscher et al., Chemische Berichten 97, 3363 (1964).
- A-nor steroids—U.S. Pat. No. 3,005,018 Laskin and Weisenborn, Bact. Proc. 26, A26 (1962).
- 17-alkyl androstanes and pregnenes—Singh et al., Can. J. of Microbiol. 13, 1271 (1967).
- androstenedione—Abdul-Hajj. Lloydia 33(2), 278 (1970).
- estradiols—Chem. Abstracts 86, 73006s (1977).

Botryodiplodia theobromae is known to be capable of 11-alpha-hydroxylating steroids (U.S. Pat. No. 3,047,470). Lasiodiplodia theobromae and Botryodiplodia theobromae are effective agents for the reduction of pyridine and of pyrimidine compounds. See for example Howe and Moore, J. Med. Chem. 14 (4), 287 (1971); British Pat. No. 1,183,850; and Howe et al., J. Med. Chem. 15, 1040 (1972). Lasiodiplodia theobromae has also been reported to oxidize mycophenolic acid. Jones et al., J. Chem. Soc. (C), 1725 (1970).

DESCRIPTION OF THE INVENTION

The present invention relates to an efficient synthesis of chenodeoxycholic acid having the structure below

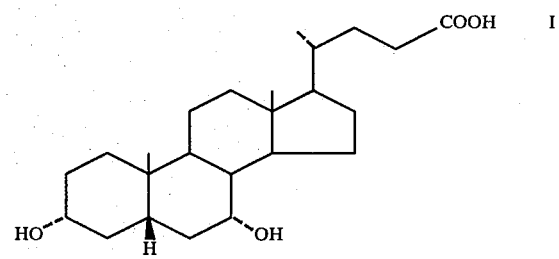

starting from 3-keto-bisnorcholenol (also named 22-hydroxy-23,24-bisnorchol-4-en-3-one) a compound of the formula:

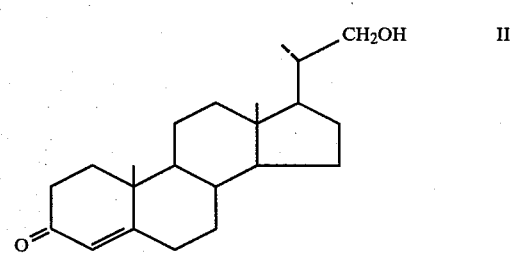

which is readily obtained by the microbiological degradation of the commercially available β-sitosterol by procedures well known to the art.

In the initial process step of the present invention 3-keto-bisnorcholenol is microbiologically hydroxylated in the 7-position to produce 7-alpha-hydroxy-3-ketobisnorcholenol (7α,22-dihydroxy-23,24-bisnorchol-4-en-3-one) of the formula:

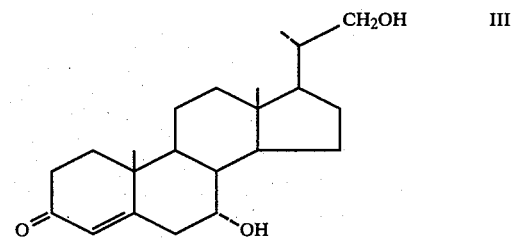

Of the 152 cultures examined for 7-alpha hydroxylation, such cultures representing 92 species in 41 genera and including many reported capable of 7-alpha hydroxylation of the various substrate compounds enumerated above, it has now been unexpectedly found that only 9 very closely related cultures, Botryodiplodia theobromae IFO 6469, ATCC 28570, DSM 62-678, DSM 62-679; Botryosphaeria ribis ATCC 22802, B. berengeriana ATCC 12557, B. rhodina CBS 374.54, CBS 287.47 and CBS 306.58, are capable of carrying out the desired 7-alpha hydroxylation on this sterol substrate.

The microorganism may be used in the form of the culture broth, the mycelia or an enzyme extract thereof. The culture broth may be prepared by inoculating the organism into a suitable medium. The culture medium can contain carbon sources, nitrogen sources, inorganic salts and other nutrients suitable for the growth of the microorganisms. The carbon sources are, for example, glucose, sucrose, dextrin, mannose, starch, lactose, glycerol and the like, the nitrogen sources are e.g. nitrogen-containing organic substances, such as peptone, meat extract, yeast extract, corn steep liquor, casein and the like, or nitrogen-containing inorganic compounds, such as nitrates, inorganic ammonium salts and the like, and the inorganic salts such as phosphates or minerals such as sodium, potassium, magnesium, manganese, iron, copper and the like.

As the cultivation method employed in this process step of the invention there can be utilized submerged culture, shaking culture, stationary culture and the like. However, since aerobic conditions are required for organisms used in this invention, it is preferable to cultivate under conditions which promote aeration.

In addition it is possible to employ in the practice of the present invention a mycelium isolated from the culture broth of the microorganisms, or a crude enzyme extracted from the culture broth or the mycelium by a known method per se can be brought into contact with the substrate under suitable conditions. In the case when such a process embodiment is adopted the 7α-hydroxylation can be conveniently performed in an aqueous solution such as a buffer solution, a physiological salt solution or a fresh medium, or in water.

The substrate compound may be added in the form of an unpalpable powder or in the form of a solution dissolved in a hydrophilic solvent such as acetone, dimethylsulfoxide, methanol, ethanol, ethylene glycol, propylene glycol, dioxane and the like. Alternatively, a surfactant or a dispersing agent may be added to a water suspension of the substrate. Furthermore, the substrate can be prepared as a finely divided suspension by treatment with ultrasonic waves.

The fermentation procedure employs conventional techniques. Thus, the desired microorganism may be grown in Edamin broth (same as fermentation medium; see below) for a period of from 18 to 72 hours at a temperature in the range of about 15° to 35° C. Fermentation is initiated by inoculating a conventional fermentation medium with from 1 to 10 wt % of the vegetative growth. The fermentation conditions can be the same as was utilized to grow the inoculum. After an incubation period of from 18 to 96 hours, the substrate bisnorcholenol is added either as a solution in, preferably absolute ethanol or as a sonically prepared solution in 0.1% Tween 80 (polyoxyethylene sorbitan monooleate). The fermentation may be carried out for up to 120 hours after addition of the substrate. A suitable fermentation medium is obtained by mixing the following or multiple thereof. Edamin (Sheffield Chemical Co.), an enzymatic digest of lactalbumin 20 grams, cornsteep liquor 3 grams, dextrose 50 grams and distilled water to a final volume of 1 liter. The pH of the medium is adjusted to about 4 to 7, preferably about 5.0 prior to sterilization e.g. by autoclaving.

Isolation of the desired 7-alpha-hydroxy-3-keto-bisnorchlorenol product from the fermentation medium is readily accomplished using procedures well known in the art. Thus, the harvested whole culture broth can be extracted with a non-miscible organic solvent such as, preferably ethyl acetate. The solvent soluble fractions may then be purified using gel chromatography such as for example with silica gel G-60, followed by crystallization.

It has further been found that a number of procedures can be employed to optimize the yield of desired product from the fermentation. Thus, for example, addition of a chelating agent such as 2,2'-dipyridyl in a final concentration ranging from $0.5 \times 10^{-4}$M to $0.75 \times 10^{-3}$M, addition with the substrate of either glucose or sucrose in a final concentration of about 5%, lowering the temperature of the incubation fermentation to about 24° C., after adding the substrate and by using a suspension of substrate at a concentration of 5% in 0.1% Tween 80. An even greater increase in yield is obtainable by the addition of adsorbants to the fermentation medium. For example yield improvement is obtained when polymeric resin absorbents such as Amberlite XAD7 (Rohm & Haas Co.), a polymer of the methyl ester of acrylic acid is added at a concentration 0.3–0.6 wt % to a fermentation medium where the substrate is present in a concentration of up to about 1 g/liter. Best yield improvement was obtained at about the 0.6 wt % concentration level for the adsorbent.

The 7-alpha-hydroxy-3-keto-bisnorcholenol produced by the above described fermentation procedure is then catalytically hydrogenated so as to produce (5β)-7α,22-dihydroxy-23,24-bisnorcholan-3-one of the formula-

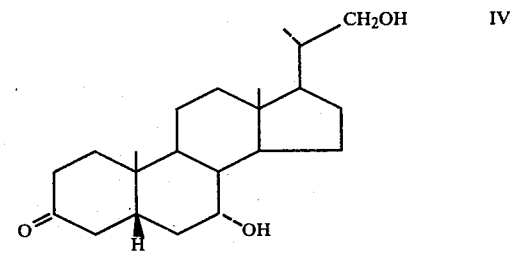

A suitable catalyst for this hydrogenation is palladium preferably on a solid support, preferably 5% palladium on charcoal. The reaction is carried out in a nonaqueous polar solvent such as dimethylformamide and at a temperature in the range of from about 0° to 50° C., preferably at about room temperature and at ambient pressure. Isolation of the product can be carried out in the same manner as from the above fermentation, i.e. gel chromatography such as with silica gel 60 and crystallization.

The saturated product of formula IV is then reacted with a p-tolyl or methyl sulfonyl halide at a temperature in the range of from 78° to 0° C., preferably at about −10° C. The reaction is conveniently carried out in a nitrogeneous organic solvent such as pyridine. A preferred reagent for this reaction is p-toluenesulfonyl chloride. The resulting product of this reaction, which can be isolated in the same manner as previously described for compounds above, has the formula

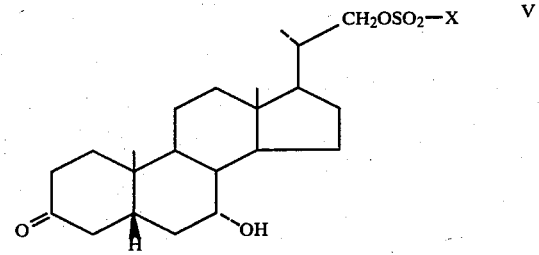

where X is methyl or p-tolyl, preferably p-tolyl.

A preferred embodiment of a compound of formula V is thus (5β)-7α-hydroxy-22-([4-methylphenyl]sulfonyl-oxy)-23,24-bisnorcholan-3-one.

In the next step of the process of the present invention a compound of formula V is reacted with sodium di-$C_{1-3}$-alkyl malonate, preferably dimethylmalonate in a polar non-aqueous solvent such as dimethylformamide at a temperature in the range of from 0° to 100° C., preferably at about 50° C. in an inert atmosphere with exclusion of moisture. The sodium di-$C_{1-3}$-alkyl malonate can be prepared in situ by adding the malonate to a solution of sodium hydride in dimethylformamide and stirring at 40°–50° C. Isolation of the end product is carried out in analogy to the procedures described previously. The resulting product has the formula

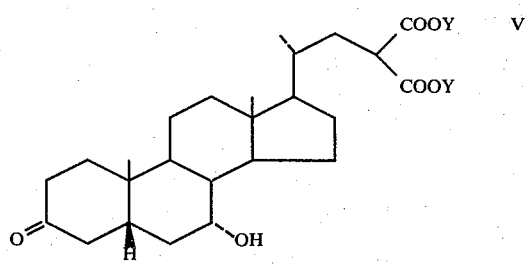

where Y is $C_{1-3}$-alkyl, preferably methyl. A preferred embodiment of a compound of formula VI is thus (5β)-24-norcholan-7α-ol-3-one-23,23-dicarboxylic acid dimethyl ester.

The compound of formula VI is then reduced to the corresponding 3-hydroxy compound of the formula

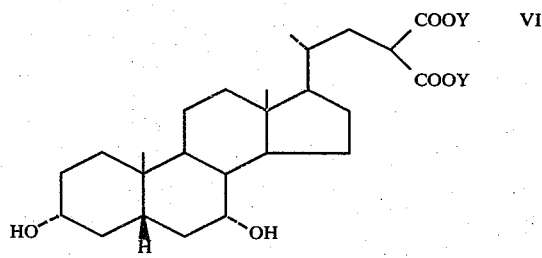

where Y is $C_{1-3}$-alkyl, preferably methyl. A preferred embodiment of a compound of formula VII is (5β)-24-norcholane-3α,7α-diol-23,23-dicarboxylic acid dimethyl ester.

The reduction procedure is accomplished by using a conventional chemical reducing agent such as sodium borohydride in an aqueous $C_{1-3}$ alkanol solvent such as 95% ethanol at a temperature in the range 0° to 50° C., preferably at room temperature under an inert atmosphere. The reaction product can be isolated from the reaction mixture by acidifying and extracting with a halocarbon solvent such as dichloroethane. Removal of the solvent provides the product in crude form which can be used without further purification in succeeding steps.

The diol of formula VII is then saponified by refluxing in the presence of strong base, i.e. barium hydroxide so as to provide, after work-up and acidification a dicarboxylic acid of the formula

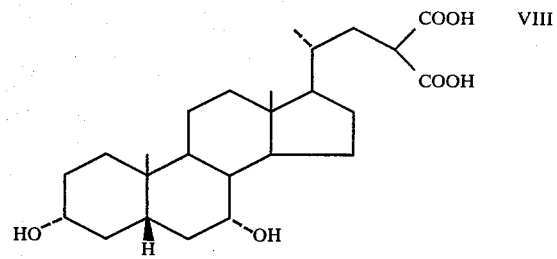

which is (5β)-24-norcholane-3α,7α-diol-23,23-dicarboxylic acid.

In the final step of this embodiment of process of the invention the dicarboxylic acid of formula VIII is thermally decarboxylated by heating the formula VIII compound at a temperature of about 190°–205° C. under an inert atmosphere so as to produce the desired end product chenodeoxycholic acid of formula I above.

In an alternate process embodiment of the present invention a compound of formula V can be treated with a chemical reducing agent such as a lithium aluminum alkoxide hydride, preferably lithium aluminum tri-t-butoxyhydride, at a temperature in the range of from about −78° C. to room temperature, preferably at about −10° C. in an inert organic solvent such as a cyclic ether, preferably tetrahydrofuran and under an inert atmosphere so as to produce a diol of the formula

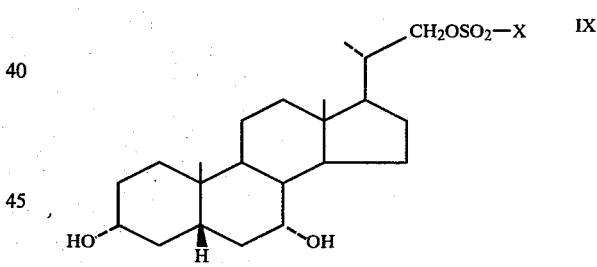

where X is as above.

A preferred embodiment of a compound of formula IX is 2,2-([4-methylphenylsulfonyl]oxy)-23,24-bisnorcholane-3α, 7α-diol.

In the next process step the compound of formula IX is reacted with a greater than twofold molar excess of an acylating agent conventionally employed as a hydroxy protecting group in steroid chemistry so as to prepare the corresponding diacyl compound. Suitable acylating agents include the $C_{2-6}$ lower alkanoic acid anhydrides, preferably acetic anhydride. The acylation is readily carried out in a suitable organic solvent such as pyridine in the presence of an amine base such as 4-dimethylaminopyridine. The resulting diacyl product has the formula:

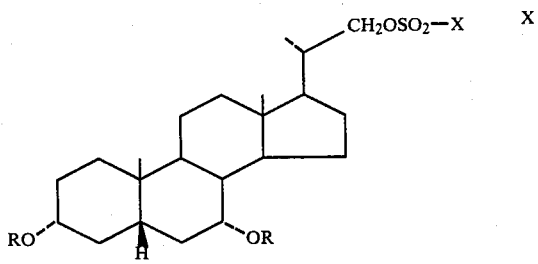

where X is as above and R is acyl.

A preferred embodiment of a compound of formula X is 22-([4-methylphenyl)sulfonyl]oxy)-23,24-bisnorcholane-3α,7α-diol 3,7-diacetate.

The diacyl compound of formula X is then reacted with a sodium di-$C_{1-3}$-alkyl malonate, preferably diethylmalonate in direct analogy to the previously described conversion of compound V to compound VI above so as to produce a compound of the following formula:

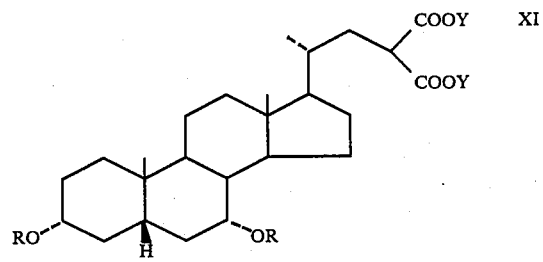

where R and Y are as above.

A preferred embodiment of a compound of formula XI is 3α,7α-(diacetoxy)-24-norcholane-23,23-dicarboxylic acid diethyl ester.

Conversion of a compound of formula XI to a dicarboxylic acid of formula VIII described above is readily accomplished by saponification with a strong base such as an alkali metal hydroxide solution, preferably potassium hydroxide at elevated temperature, preferably at reflux. The reaction can be carried out in the presence of one or more lower alkanols as solvent such as, for example methanol, isopropanol or mixtures thereof.

The process and intermediates of the present invention are further illustrated by reference to the following Examples.

EXAMPLE 1

(5β)-7α,22-Dihydroxy-23,24-bisnorchol-4-en-3-one (7-alpha-OH-3-KC)

Fermentation Procedures

Cultures were maintained on the following media: bacteria, glucose nutrient agar; fungi, Sabouraud Dextrose agar (SD) (Difco); actinomycetes, starch-casein agar. Vegetative inoculum was prepared in either Sabouraud Dextrose broth (Difco) or in the medium used in the fermentation stage. The latter was composed of: Edamin (Sheffield Chemical Co.), 20 g; cornsteep liquor (Corn Products Co.), 3 g.; dextrose, 50 g.; and distilled water to a final volume of 1 liter. The pH was adjusted to 5.0 with HCl prior to sterilization by autoclaving. The fermentations were carried out either in 250 or 500 ml Erlenmeyer flasks containing 50 and 100 ml of medium respectively. The flasks were inoculated with vegetative growth (5%) from cultures grown in the inoculum medium for 72 hours at 28° C. on a 250 RPM rotary shaker (5 cm eccentricity). Unless otherwise indicated, the same conditions apply for the fermentation stage. The 3-keto-bisnorcholenol (3-KC) was added after 48 hour incubation either as a solution in 3A ethanol, or as a 5% suspension in 0.1% solution of Tween 80 (Atlas Chemical Industries) prepared by sonic treatment (Bronson Sonifier Cell Disruptor 200). Incubation was continued for up to 120 hours after addition of the substrate.

Seventy-five species of fungi representing thirty-two genera, six species of actinomycetes, representing five genera, and eight species of gram-negative bacteria belonging to three genera, and three species of Gram positive bacteria belonging to one genus (152 cultures in total), were tested for their ability to convert 3-KC to 7-alpha-OH-3-KC. As a result of this screening, only nine cultures were found capable of the desired transformation. Other members of these same genera, and, in some cases, other strains of the same species, appeared to be incapable of converting the substrate to the desired product (Table 1).

| Culture | Source Code | 7-α-OH-3-KC |
|---|---|---|
| Botryodiplodia theobromae | IFO 6469 | + |
| Botryodiplodia theobromae | DSM 62-678 | + |
| Botryodiplodia theobromae | DSM 62-679 | + |
| Lasiodiplodia theobromae (Botryodiplodia theobromae) | ATCC 28570 | + |
| Lasiodiplodia theobromae (Diplodia natalensis) | ATCC 9055 | 0 |
| Lasiodiplodia theobromae (Diplodia theobromae) | ATCC 10936 | 0 |
| Lasiodiplodia theobromae (Botryodiplodia theobromae) | ATCC 16931 | 0 |
| Lasiodiplodia theobromae (Botryodiplodia theobromae) | ATCC 26123 | 0 |
| Diplodia natalensis | ATCC 9055 | 0 |
| Diplodia zeae | QM 6983 | 0 |
| Botryodiplodia malorum | CBS 134.50 | 0 |
| Botryosphaeria ribis | ATCC 22802 | + |
| Botryosphaeria berengeriana | ATCC 12557 | + |
| Botryosphaeria rhodina | CBS 374.54 | + |
| Botryosphaeria rhodina | CBS 287.47 | + |
| Botryosphaeria rhodina | CBS 306.58 | + |
| Botryosphaeria corticis | ATCC 22927 | 0 |

Shake flask experiments on Botryodiplodia theobromae IFO 6469 indicated that product yields were increased by addition of 2,2'-dipyridyl, a chelating agent, to final concentrations ranging from $0.5 \times 10^{-4}$M to $0.75 \times 10^{-3}$M.

Also, it was noted that at the time of substrate addition, 48 h., the culture was depleted of the glucose originally present. Addition of either glucose or sucrose (final concentration 5%) at this time appeared to slow degradation of 3-KC and 7-alpha-OH-3-KC. Other small improvements in yield were also achieved by lowering the temperature to 24° C. at 48 h., and by using a 5% suspension of substrate prepared by sonic treatment in 0.1% Tween 80. By combining all of these improved conditions, a 25% conversion of 3-KC to 7-alpha-hydroxy-3-KC was achieved with 46% of unreacted 3-KC still present (analyses by high pressure liquid chromatography (HPLC)).

The most striking improvement in yield was found as a result of addition of absorbants to the fermentation. When Amberlite XAD-7 was added at 0.3-0.6% to fermentations of Botryodiplodia theobromae IFO 6469 strain, a substantial increase in the yield of 7-alpha-OH-3-KC resulted. This increase of product formation was evident at 3-KC concentrations of up to 1 g/liter; at higher substrate concentrations XAD-7 was without effect. Similarly, no further stimulation of yields were obtained with XAD-7 in amounts above 0.6%. Before use, the XAD-7 resin was refluxed in acetone for 2½ hours, rinsed repeatedly with distilled water until all traces of acetone and color were gone, and dried at 40° C.

The 7-alpha-hydroxylation of 3-KC was also carried out with the said *Lasiodiplodia theobromae* culture with minor modifications of the basic fermentation procedures. HPLC analyses of an extract of a fermentation carried out with this organism indicated a 25% yield with 22% of remaining substrate.

Identification of the transformation product of 3-KC was performed on material isolated from both cultures as described below.

Isolation of 7-alpha-OH-3-KC

Two liters of harvested whole culture broth from a fermentation which had been charged with 1 gram of 3-KC, was extracted twice, each time with 1 liter of ethyl acetate. The extracts were combined, concentrated to 0.5 liter and filtered through glass wool. The filtrate was evaporated to dryness and the residue redissolved in 150 ml of hot ethyl acetate. After cooling to room temperature an insoluble fraction was again removed by filtration. The filtrate was concentrated by evaporation to 35 ml and applied to a 29 mm dia. column containing 200 g of silica gel G-60. The column was developed with ethyl acetate and the 7-alpha-OH-3-KC rich fractions combined, concentrated and rechromatographed on silica gel G-60 developed with methylene chloride, ethyl acetate, hexane (1:1:1). The 7-alpha-OH-3-KC rich fractions were again combined, the solvent removed by evaporation and the product obtained by crystallization from a small volume of ethyl acetate (220 mg from the Botryodiplodia culture; 185 mg from the Lasiodiplodia culture). Identity as 7-alpha-OH-3-KC was established by comparison with an authentic synthetic sample of 7-alpha-OH-3-KC: m.p. 199°–200° C. (authentic sample 197.5°–200° C.); mixture m.p. (undepressed); NMR, mass spectrum and specific rotation.

Analyses

Unless otherwise indicated, quantitative analyses for 3-KC and 7-alpha-OH-3-KC were by thin-layer chromatography (TLC). These were carried out on ethyl acetate extracts of fermentation samples. The extracts were evaporated to dryness at 40° C. and redissolved in a volume of 3A ethanol ten times smaller than the original sample volume. Chromatography was on silica gel $F_{254}$ TLC plates (E. Merck, Darmstadt, Germany) developed with ethyl acetate. The developed plates were air-dried and the spots visualized under short wavelength UV light (254 nm). The $R_f$ values obtained in this TLC system were 0.75 and 0.36 for substrate and product respectively. Minor amounts of products having $R_f$ values lower than 0.36 can be seen in the chromatogram, and their separation from the desired product can be improved by repeated development with the same solvent system.

Quantitative assays of the materials in the spots were made by carefully scraping the area of the spot from the plate into a test tube, and eluting overnight with 5 ml of 3A ethanol. The absorbance of the eluate was measured at 240 nm in a Gilford 250 spectrophotometer, and compared with values from a standard curve obtained by chromatographing known amounts of authentic 3-KC and 7-alpha-OH-3-KC. TLC results were also quantitated by measuring fluorescence quenching of the spots (Zeiss TLC Spectrophotometer, PMQII).

High pressure liquid chromatographic HPLC) analyses were carried out on a silica gel (SR-I-10) column developed with 20% dioxane in methylene chloride. The column was monitored with a 254 nm detector.

EXAMPLE 2

(5β)-7α,22-Dihydroxy-23,24-bisnorcholan-3-one

To 1.92 g (0.0055 mol) of 7α,22-dihydroxy-23,24-bisnorchol-4-en-3-one dissolved in 25 ml of freshly distilled, dry dimethylformamide was added 0.19 g of 5% palladium on carbon. The suspension was stirred under a hydrogen atmosphere at room temperature for 5.5 hr. Hydrogen uptake ceased at 108 ml (theory 124 ml). The catalyst was removed by filtration and was washed with 200 ml of ethyl acetate. The filtrate was poured into 1 l. of water and was extracted with 5×250 ml of ethyl acetate (saturated brine was added to aid break-up of emulsions). The combined ethyl acetate extracts were washed with 5×250 ml of water followed by 2×250 ml of saturated sodium chloride. The ethyl acetate was dried over sodium sulfate and evaporated in vacuo to give 2.13 g of crude (5β)-7α,22-dihydroxy-23,24-bisnorcholan-3-one. The total product was chromatographed on 150 g of silica gel 60 and eluted with ethyl acetate. The product fraction weighing 1.7 g was rechromatographed on 300 g of silica gel 60 and eluted with a solvent mixture of ethyl acetate/methylene chloride (2:1) giving 1.29 g (67%) of (5β)-7α,22-dihydroxy-23,24-bisnorcholan-3-one. The analytical sample was crystallized from ethyl acetate, mp 132°–133° C.

$[\alpha]^{25}D = +15.4$ (c 1.01, CHCl$_3$).

Calc for $C_{22}H_{36}O_3$: C, 75.82; H, 10.41, Found: C, 76.10; H, 10.69.

EXAMPLE 3

(5β)-7α-Hydroxy-22-([(4-methylphenyl)sulfonyl]-oxy)-23,24-bisnorcholan-3-one

To 1.0 g (0.00286 mol) of (5β)-7α,22-dihydroxy-23,24-bisnorcholan-3-one dissolved in 20 ml of absolute pyridine cooled to −10° C. was added 2.18 g (0.0114 mol) of p-toluenesulfonyl chloride. The solution was stirred for 1 hr at −10° C. and then placed in a refrigerator overnight. The reaction was then poured into 400 ml of a 0.25 N sodium bicarbonate solution and extracted with 4×100 ml of ethyl acetate. The combined ethyl acetate extracts were washed successively with 3×100 ml of 1 N sodium bicarbonate, 3×100 ml of water, 3×100 ml of 1 N hydrochloric acid, and finally with water until neutral. After drying with sodium sulfate, the ethyl acetate was evaporated to give 1.54 g of crude product which was purified by column chromatography on 150 g of silica gel 60. Elution with benzene/ethyl acetate (4:1) gave 1.15 g (80% yield) of (5β)-7α-hydroxy-22-([(4-methylphenyl)sulfonyl]-oxy)-23,24-bisnorcholan-3-one. The analytical sample was recrystallized from toluene/heptane, mp 157°–160° C., $[\alpha]^{25}D + 12.7$ (c 0.994, CHCl$_3$).

Anal. Calcd: C, 69.29; H, 8.42, Found: C, 69.55; H, 8.47.

EXAMPLE 4

(5β)-24-Norcholan-7α-ol-3-one-23,23-dicarboxylic acid dimethyl ester

To 3 of dry dimethylformamide at room temperature under an argon atmosphere was added 30 mg (0.0007 mol) of 57% sodium hydride followed by 0.066 g (0.0005 mol) of dimethyl malonate dissolved in 1 ml of dimethylformamide. After stirring for 1.5 hr at 40°–50° C., 0.251 g (0.0005 mol) of (5β)-7α-hydroxy-22-([(4-methylphenyl)sulfonyl]-oxy)-23,24-bisnorcholan-3-one was added. The reaction was stirred for 1 hr at room temperature, warmed to 50° C. in an oil bath for 18 hr, and then poured into 25 ml of water. Extraction with 4×10 ml of ethyl acetate followed by washes with water and saturated brine gave, after drying over sodium sulfate and evaporation, 0.20 g of crude product. After chromatography on 20 g of silica gel 60 and elution with a mixture of dichloromethane/ethyl acetate (2:1), 0.041 g (17% yield) of (5β)-24-norcholan-7α-ol-3-one-23,23-dicarboxylic acid dimethyl ester was obtained.

EXAMPLE 5

(5β)-24-Norcholane-3α,7α-diol-23,23-dicarboxylic acid dimethyl ester

To a solution of 0.195 g (0.00042 mol) of (5β)-24-norcholan-3-one-23,23-dicarboxylic acid dimethyl ester in 12 ml of 95% ethanol at room temperature under an argon atmosphere was added 0.025 g (0.00063 mol) of sodium borohydride. The reaction mixture was allowed to stir for 2 hrs, then poured into 50 ml of water containing 4 ml of 1 N hydrochloric acid. The aqueous solution was extracted with dichloromethane and the combined extracts dried over sodium sulfate and evaporated to give 0.195 g of the above-captioned crude diol.

EXAMPLE 6

(5β)-24-Norcholane-3α,7α-diol-23,23-dicarboxylic acid

To a solution of 0.195 g of crude (5β)-24-norcholane-3α,7α-diol-23,23-dicarboxylic acid dimethyl ester in 5 ml of ethanol was added 2 ml of water followed by 0.80 g of barium hydroxide. The solution was heated at reflux for 3 hrs, cooled to room temperature, and then acidified by the addition of 1 N hydrochloric acid. After extraction with dichloromethane and drying, the solvent was evaporated to give 0.135 g of (5β)-24-norcholane-3α,7α-diol-23,23-dicarboxylic acid.

EXAMPLE 7

Chenodeoxycholic Acid

In a round-bottom flask under an argon atmosphere, 0.135 g (0.00031 mol) of (5β)-24-norcholane-3α,7α-diol-23,23-dicarboxylic acid was heated for 10 min at 190°–205° C. Gas evolution was observed. After cooling, the residue was chromatographed on 10 g of silica gel 60 and eluted with 10% ethanol in ethyl acetate to give 0.045 g of chenodeoxycholic acid as a glass. Tlc and nmr were identical with an authentic sample.

EXAMPLE 8

22-([[(4-methylphenyl)sulfonyl]oxy)-23,24-bisnorcholane-3α,7α-diol

To 0.350 g (0.00069 mole) of (5β)-7α-hydroxy-22-([(4-methylphenyl)sulfonyl]oxy)-23,24-bisnorcholan-3-one in 10 ml of dry tetrahydrofuran cooled to −10° C. under an argon atmosphere is added dropwise 0.391 g (0.00138 mole) of lithium aluminum tri-t-butoxyhydride dissolved in 5 ml of dry tetrahydrofuran. After 1½ hr, the reaction was quenched by the addition of 2 ml of 1 N hydrochloric acid. The tetrahydrofuran was removed in vacuo. The residue was taken up in 50 ml of water and extracted with 3×40 ml of ethyl acetate. The combined ethyl acetate extracts were washed with water until neutral and dried over anhydrous sodium sulfate. The mixture was filtered and solvent removed in vacuo to give 0.374 g of crude product. This was chromatographed on 37 g of silica gel 60 and eluted with ethyl acetate to give 0.290 g (88%) of 22-([[(4-methylphenyl)sulfonyl]oxy)-23,24-bisnorcholane-3α,7α-diol.

The analytical sample was recrystallized from isopropanol/water. Mp 87°–89° C.

$[\alpha]^{25}D = +8.25$ (c 0.9933, CHCl$_3$).

Calcd. for $C_{29}H_{44}O_5S$: C, 69.01; H, 8.79; S, 6.35, Found: C, 69.21; H, 8.88; S, 6.07.

EXAMPLE 9

22-([[(4-methylphenyl)sulfonyl]oxy)-23,24-bisnorcholane-3α,7α-diol 3,7-diacetate A mixture of 0.290 g (0.00049 mole) of 22-([[(4-methylphenyl)sulfonyl]oxy)-23,24-bisnorcholane-3α,7α-diol, 0.6 ml (0.0064 mole) of acetic anhydride, 0.6 ml (0.0074 mole) of dry pyridine, 0.003 g (0.000025 mole) of 4-dimethylaminopyridine, and 10 ml of dry toluene was stirred overnight under an argon atmosphere. The mixture was acidified with 50 ml of 0.5 Normal hydrochloric acid and extracted with 3×20 ml of ethyl acetate. The ethyl acetate extracts were washed with water until neutral, then dried over anhydrous sodium sulfate. The mixture was filtered and solvent removed in vacuo to give 0.311 g of crude product. This was recrystallized from methanol to give as a first crop material 0.2577 g (76%) of 22-([[(4-methylphenyl)sulfonyl]oxy)-23,24-bisnorcholane-3α,7α-diol 3,7-diacetate. The mother liquor, after evaporation gave 0.065 g (19%) of product which by tlc appeared to be greater than 95% pure. The analytical sample was recrystallized from methanol. Mp 174°–175° C.

$[\alpha]^{25}D + 7.41$ (c 0.8768, CHCl$_3$).

Calcd for $C_{33}H_{48}O_7S$: C, 67.32; H, 8.22, Found: C, 67.34; H, 8.33.

EXAMPLE 10

3α,7α-(diacetoxy)-24-norcholane-23,23-dicarboxylic acid diethyl ester 0.264 g (0.0055 mole) of a 50% oil dispersion of sodium hydride was washed under an argon atmosphere with 3×3 ml of dry pentane. Then, 7.5 ml of dry toluene was added. 1.056 g (0.0066 mole) diethylmalonate in 5 ml of dry toluene was added dropwise, then heated to reflux and 1.1776 g (0.0020 mole) of 22([[(4-methylphenyl)sulfonyl]oxy)-23,24-bisnorcholane-3α,7α-diol 3,7-diacetate in 10 ml of dry toluene was added dropwise. The mixture was heated to reflux for 20 hours. An additional 0.49 g (0.003 mole) of diethylmalonate and 0.050 g (0.001) mole of washed (pentane) sodium hydride was added and the mixture heated to reflux. After five hours, the cooled mixture was poured into 100 ml of water and extracted with 3×60 ml of ethyl acetate. The combined ethyl acetate extracts were washed with water until neutral and dried over anhydrous sodium sulfate. The mixture was filtered and solvent removed in vacuo leaving a 1.114 g residue. This was chromatographed on 100 g of silica gel 60 and eluted with methylene chloride/ethyl acetate (9:1) to give 0.849 g (76%) of 3α,7α-(diacetoxy)-24-norcholane-23,23-dicarboxylic acid diethyl ester. The analytical sample was recrystallized from methanol/water. Mp 121.5°–123° C.

$[\alpha]^{25}D + 23.97$ (c 1.0679, CHCl$_3$).

Calcd for $C_{33}H_{52}O_8$: C, 68.72; H, 9.09, Found: C, 68.92; H, 9.00.

EXAMPLE 11

3α,7α-Dihydroxy-24-norcholane-23,23-dicarboxylic acid

To a solution of 3 ml of methanol, 5 ml of isopropanol and 0.779 g (0.0139 mole) of potassium hydroxide is added 0.350 g (0.0006 mole) of 3α,7α-(diacetoxy)-24-norcholane-23,23-dicarboxylic acid diethyl ester. The mixture was heated to reflux under an argon atmosphere for 4 hrs then left to stir overnight at room temperature. The alcohol solvents were removed in vacuo and the mixture poured into 50 ml of water and washed with 3×25 ml of diethyl ether. The aqueous layer was acidified and the precipitate collected by suction filtration. 0.252 g (96%) of the crude diacid was obtained, Mp 203° C., with decomposition. This was used directly in the next step without further purification.

EXAMPLE 12

Chenodeoxycholic Acid

A mixture of 0.125 g (0.00028 mole) of 3α, 7α-dihydroxy-24-norcholane-23,23-dicarboxylic acid, 5 ml of xylene and 1 ml of dry pyridine was heated to reflux for one hour. The mixture was cooled, solvents were removed in vacuo and the residue dissolved in 25 ml of ethyl acetate. The ethyl acetate solution was washed with 3×10 ml of 1 N hydrochloric acid, then with water until neutral. The ethyl acetate extract was dried over anhydrous sodium sulfate, filtered and solvent removed in vacuo to give 0.111 g of crude product. This was recrystallized from hexane/ethyl acetate to give (first crop material), 0.086 g (76%) of product which had the same spectral properties as authentic chenodeoxycholic acid and gave no melting point depression. An analytical sample was prepared by chromatography on silica gel 60 eluting with methylene chloride/methanol/hexane, (2:1:1), then recrystallized from ethyl acetate.

We claim:

1. A process for the preparation of 7-alpha-hydroxy-3-keto-bisnorcholenol which process comprises 7-alpha-hydroxylating 3-keto-bisnorcholenol by contacting said 3-keto-bisnorcholenol with a microorganism selected from the group consisting of *Botryodiplodia theobromae* IFO 6469, DSM 62-678, DSM 62-679; *Lasiodiplodia theobromae* ATCC 28570; *Botryosphaeria ribis* ATCC 22802, *B. berengeriana* ATCC 12557, *B. rhodina* CBS 374.54, CBS 287.47 and CBS 306.58, said microorganism being in the form of a culture broth, mycelia or an enzyme extract thereof.

2. The process of claim 1 wherein an adsorbent is present during said 7alpha-hydroxylation.

3. The process of claim 2 wherein said adsorbent is a polymer of the methyl ester of acrylic acid present in a final concentration of 0.3 to 0.6 wt % and said 3-keto-bisnorcholenol is present in a concentration of up to about 1 g/liter.

4. The process of claim 1 wherein a chelating agent is present during 7-alpha-hydroxylation.

5. The process of claim 4 wherein said chelating agent is 2,2'-dipyridyl.

* * * * *